United States Patent [19]
Matsumoto et al.

[11] Patent Number: 6,098,465
[45] Date of Patent: Aug. 8, 2000

[54] MATERIAL TESTING MACHINE INCLUDING A CONTROL SYSTEM FOR FEEDBACK-CONTROLLING THE OPERATION OF A SERVO SYSTEM

[75] Inventors: Masayuki Matsumoto; Nobunari Takahashi, both of Toyohashi; Susumu Kamio; Tatsuyoshi Kotou, both of Kitakyushu, all of Japan

[73] Assignee: Japan Tobacco Inc., Tokyo, Japan

[21] Appl. No.: 09/133,369

[22] Filed: Aug. 13, 1998

[30] Foreign Application Priority Data

Aug. 13, 1997 [JP] Japan .................................... 9-218550
Aug. 13, 1997 [JP] Japan .................................... 9-218553

[51] Int. Cl.$^7$ .................................................... G01N 3/32
[52] U.S. Cl. .............................................................. 73/808
[58] Field of Search ............................ 73/788, 790, 797, 73/798, 807, 808, 804

[56] References Cited

U.S. PATENT DOCUMENTS

| | | | |
|---|---|---|---|
| 3,664,179 | 5/1972 | Danko et al. ............................... | 73/805 |
| 4,176,396 | 11/1979 | Howatt ....................................... | 73/104 |
| 5,299,459 | 4/1994 | Underwood . | |
| 5,406,842 | 4/1995 | Locke ..................................... | 73/290 R |

FOREIGN PATENT DOCUMENTS 1385461  2/1975  United Kingdom .

OTHER PUBLICATIONS

Patent Abstracts of Japan, JP 03 248033 A, Jan. 31, 1992, vol. 016, No. 042.
Patent Abstracts of Japan, JP 09 138188 A, Sep. 30, 1997, vol. 1997, No. 09.
Patent Abstracts of Japan, JP 09 203700 A, Dec. 25, 1997, vol. 1997, No. 12.
PatentAbstracts of Japan, JP 59 182603 A, Feb. 22, 1985, vol. 009, No. 043.
Patent Abstracts of Japan, JP 63 241443 A, Feb. 3, 1989, vol. 013, No. 047.

*Primary Examiner*—Max Noori
*Attorney, Agent, or Firm*—Birch, Stewart, Kolasch & Birch, LLP

[57] ABSTRACT

A material testing machine includes a control system which, during material testing, feedback-controls the operation of a servo system which includes an actuator for applying a load to a test piece, such that the actual load applied to the test piece coincides with the target load. The testing machine includes a waveform generator for generating a testing waveform indicative of the target load. The waveform generator includes a waveform data memory which stores therein a series of basic signal values sampled from a basic waveform so as to pick up a characteristic of the basic waveform. During the material testing, each of the basic signal values is repeatedly read out from the data memory, whereby the testing waveform indicating the target load is generated based on these basic signal values. An error between the controlled variable and the target load is determined based on peak and bottom values of the controlled variable, and the target load is corrected in accordance with the determined error, to thereby improve the responsiveness of the servo system.

5 Claims, 8 Drawing Sheets

MATERIAL TESTING MACHINE INCLUDING A CONTROL SYSTEM FOR FEEDBACK-CONTROLLING THE OPERATION OF A SERVO SYSTEM

BACKGROUND OF THE INVENTION

1. Technical Field

The present invention relates to a material testing machine, and more particularly, to an electrohydraulic servo-controlled material testing machine.

2. Related Art

An electrohydraulic servo-controlled material testing machine is known which is comprised of a controller for supplying, via a servo amplifier, an electric signal input to an electrohydraulic servo valve provided between a hydraulic power source and a hydraulic actuator such as hydraulic cylinder, the electric signal input varying in accordance with a target displacement of a movable part of the actuator. Typically, the quantity of fluid output from the servo valve varies in response to the electric signal input, and the movable part of the hydraulic cylinder is displaced at a speed proportional to the fluid quantity, whereby a load is applied to a test piece held between the cylinder movable part and a main body of the testing machine. An actual displacement of the cylinder movable part is detected and is supplied as a feedback signal to the controller. Under the control of the controller, a feedback control is carried out to cause the actual displacement to close to a target displacement.

In this specification, the term "displacement of a test piece" indicates the displacement of one end of the test piece coupled to a movable part of an actuator which displacement is caused by the displacement of the movable part of the actuator. In a material testing machine of a type provided with two actuators whose movable parts hold a test piece therebetween are typically displaced in opposite directions, the term "displacement of the test piece" indicates the sum of displacements of opposite ends of the test piece caused by the displacement of the two movable parts of the actuators. That is, the term "displacement of the test piece" indicates deformation of the test piece caused by the displacement of the movable part(s) of the actuator.

The term "servo system" indicates a system mainly comprised of an actuator, a servo amplifier, and a servo valve. The term "control system" indicates a system mainly comprised of a servo system and a controller for controlling the operation of the servo system. The term "control loop" or "feedback control loop" indicates a loop mainly comprised of a servo system, a controller, and a test piece. Moreover, the term "force control system" indicates a control system for carrying out a feedback control with use of an actual force applied to the test piece, as the controlled variable, whereas the term "displacement control system" indicates a system for executing a feedback control using, as a controlled variable, an actual displacement of the test piece. The term "load" indicates a broadly defined load which includes a force applied to the test piece and generally referred to as a load, and which also includes the displacement of the test piece. If that the actual load or the actual displacement is referred to as a controlled variable, the term "control objective value" or "control target value" indicates a target load.

The material testing machine sometimes carries out a fatigue test in which mechanical properties of a test piece are measured while the load given to the test piece is periodically changed. For example, the actual force applied to and the actual displacement of the test piece are measured while the target load, e.g., the target force applied to the controller of the testing machine periodically changes in a specific pattern such as sinusoidal a wave, triangular wave, rectangular wave or ramp wave. On this occasion, under the feedback control of the control system, the actual force generally changes following the variable target force. As the repetitive frequency of the target force, inversely proportional to the cycle of the target force changing pattern, becomes higher, the followingness of the actual force to the target force is deteriorated, causing the testing accuracy to be lowered.

At the occasion of a fatigue test, a testing waveform indicative of the target force which periodically varies in specific patterns is given to the servo control system of the testing machine. The amplitude and repetition cycle of the testing waveform are set so as to be suited to the kind or size of the test piece or the kind or purpose of material testing. For instance, in the case of a fatigue test, the repetitive frequency of the testing waveform varies, depending on the testing purpose, within a range from a very low frequency in the order of 0.01 Hz to a certain frequency in the order of 100 Hz which is an operational upper limit of hydraulic servo system.

A waveform generator for generating, in an analog fashion, various types of testing waveform, especially a testing waveform which varies at very low frequency, is generally extremely high in cost and is complicated in construction. Thus, various attempts have been made to generate a variety of testing waveforms in a digital fashion. However, this requires a memory of large capacity for storing therein waveform data based on which various types of testing waveform are generated, or requires considerably complicated operation for generating a testing waveform with high accuracy.

SUMMARY OF THE INVENTION

An object of the present invention is to provide a material testing machine capable of compensating for a follow-up delay of actual an load to target load even if the repetition frequency at which the target load varies in a specific pattern is high, thereby accurately performing a fatigue test.

Another object of the present invention is to provide a material testing machine capable of easily generating a testing waveform which gives a target load suited to the purpose of material testing.

According to one aspect of the present invention, there is provided a material testing machine for measuring a mechanical property of a test piece based on a load given to the test piece and a mechanical change (e.g., displacement or distortion) generated in the test piece, while feedback-controlling an operation of a servo system, including a hydraulic actuator which gives the load to the test piece, by means of a controller, such that an actual load applied to the test piece coincides with a target load.

The material testing machine comprises: load control means for periodically changing a target load in the feedback control to thereby periodically change a load given to the test piece; error detection means for determining an error between a target load and a controlled variable in the feedback control, based on a peak value and a bottom value of the controlled variable which changes with a change in the load; and correction means for correcting the target load in accordance with the error determined by the error detection means.

With this testing machine, the error between the controlled variable and the target load is determined based on the peak and bottom values of the controlled variable, and the target load per se is corrected in accordance with the determined error, whereby the deteriorated control response of the servo system which is liable to occur especially if the target load changing cycle is short can be compensated. This makes it possible to cause the actual load to appropriately follow the variable target load, irrespective of whether the target load changing cycle is long or short in time length, whereby accurate material testing can be achieved.

Preferably, the error detection means determines an amplitude of the controlled variable based on the peak and bottom values of the controlled variable, for every target load changing cycle, and then determines the error between the controlled variable and the target load based on the amplitude of the controlled variable and an amplitude of the target load.

With this preferred arrangement, it is possible to correct the target load for every target load changing cycle based on the error determined in the cycle concerned, whereby the control response of the servo system can be securely improved.

According to another aspect of this invention, a material testing machine comprises a waveform generator for generating a testing waveform which indicates a target load in the feedback control. The waveform generator includes: a waveform data memory storing therein a series of basic signal values which are sampled from a basic waveform so as to pick up a characteristic of the basic waveform; waveform data reading means for reading out the series of basic signal values from the waveform data memory and for repetitively reading out at least one basic signal value a repetitive number of times which is determined by a thinning number, to thereby obtain temporary signal values; thinning compensation means for correcting, in accordance with the thinning number, those temporary signal values which do not correspond to any of sampling points at which the basic signal values are sampled from the basic waveform, to thereby obtain a temporary testing waveform which is similar in shape to the basic waveform; and testing waveform generator means for adjusting an amplitude of the temporary testing waveform to thereby obtain a testing waveform.

With this testing machine, typically, a testing waveform serving as a target load which periodically varies is generated. In such a typical case, the testing waveform has its one cycle part which is comprised of signal values which are greater in number than a series of basic signal values constituting one cycle part of the basic waveform. On an occasion that the series of basic signal values are read out from the waveform data memory, each of the basic signal values is repeatedly read out a repetitive number of times, corresponding to a thinning number, to thereby obtain temporary signal values. Desired ones of these temporary signal values are corrected to obtain a temporary testing waveform from which the testing waveform having frequency and amplitude suited to a testing purpose is generated. Accordingly, various types of testing waveform, especially a testing waveform having a very low frequency, can be easily efficiently generated with accuracy, without the need of using a waveform data memory of a large capacity.

Preferably, the waveform data memory stores a series of basic signal values which constitute one cycle part of the basic waveform. The thinning number is set in accordance with a number of times of sampling the series of basic signal values from the basic waveform, the frequency of the testing waveform, and the cycle at intervals of which the waveform reading means reads out the basic signal values. The thinning compensation means obtains the temporary testing waveform which has the same frequency as that of the testing waveform.

With this preferred arrangement, the testing waveform which periodically varies in a specific pattern, such as a sinusoidal wave or a triangular wave, can be generated without the need of using a waveform data memory of a large capacity.

Preferably, the thinning compensation means corrects each of the temporary signal values which do not correspond the sampling points of the basic waveform, based on a compensation value which is determined in accordance with the thinning number and the difference between two temporary signal values associated therewith among the temporary signal values corresponding to the sampling points of the basic waveform.

With this preferred arrangement, those temporary signal values which do not correspond to the sampling points of the basic waveform can be corrected in such a manner that they are suited to constitute the temporary testing waveform.

Preferably, the waveform generator further includes testing waveform level setting means for variably setting a level of an average value of the testing waveform in accordance with the controlled variable fed back to the controller.

With this preferred arrangement, the testing waveform suited to the control response characteristic of the servo system can be obtained.

These and other features and advantages will be more apparent from a detailed description of particular embodiments of this invention illustrated as non-exclusive examples in the appended drawings.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION

With reference to the appended drawings, an electrohydraulic servo-controlled material testing machine according to an embodiment of the present invention will be explained.

Figure 1:
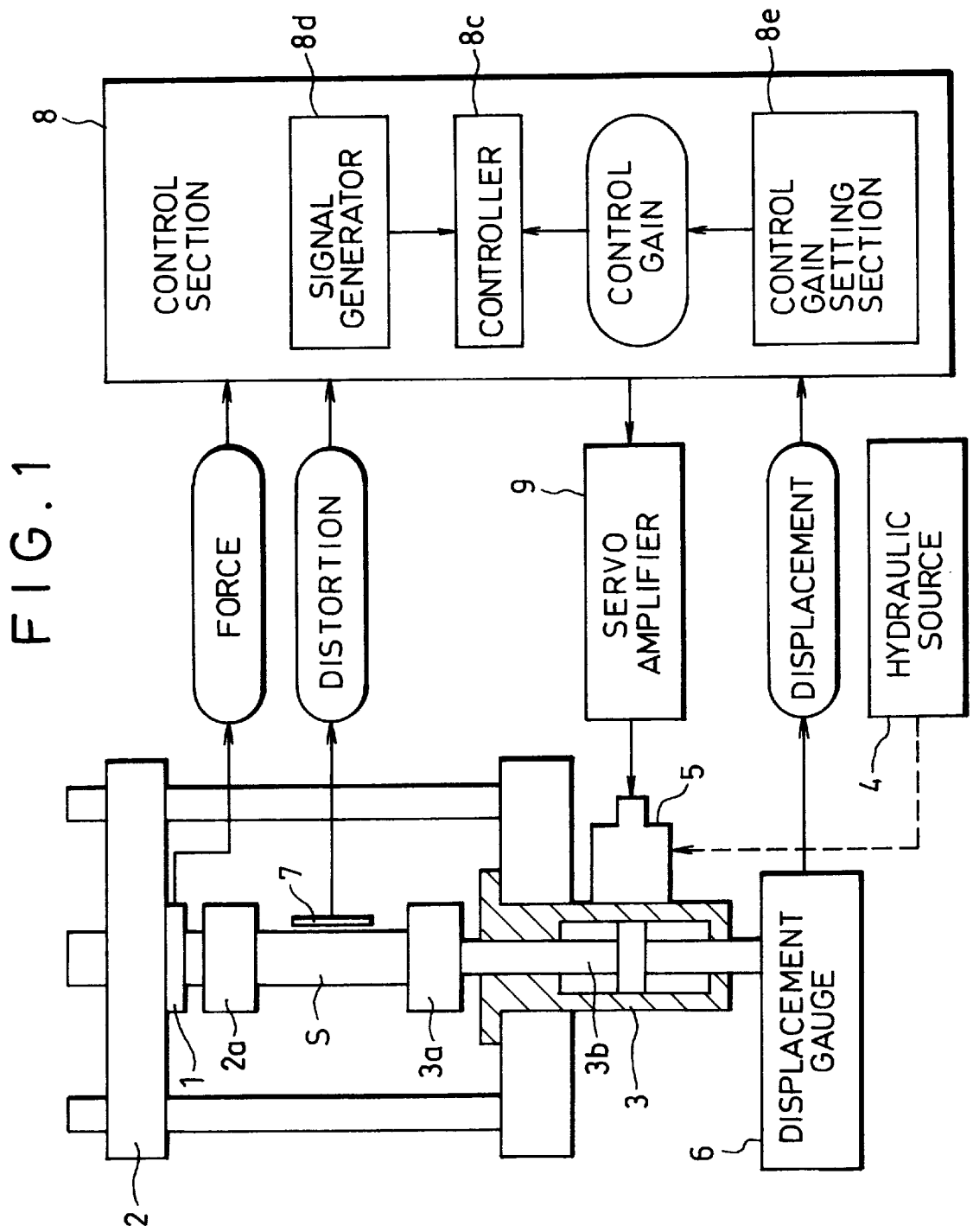
FIG. 1 is a schematic view showing the basic construction of a material testing machine according to an embodiment of the present invention.

As shown in FIG. 1, the testing machine is so configured as to supply a pressurized fluid (fluid pressure) from a hydraulic source 4 to an actuator 3, comprised of a hydraulic cylinder, through a servo valve 5 to operate a movable rod 3b of the actuator 3, thereby providing a load to a test piece S which is held between a stationary chuck 2a provided on the side of a frame of a machine body and a movable chuck 3a provided on the actuator-side. Depending on the type of material testing, the stationary chuck 2a may be removed and a die may be provided instead of the movable chuck 3a, so as to attach the test piece S between the die 3a and a load cell 1.

An actual force applied to the test piece S from the movable rod 3b is detected by the load cell 1, displacement of the test piece S is detected by a displacement gauge 6, and distortion of the test piece S is detected by a distortion gauge 7 attached to the test piece. A controller 8c of a control section 8 which is comprised of a microcomputer and the like inputs the detected force, displacement and distortion, and controls the operation of the servo valve 5 via a servo amplifier 9 in a feedback manner, with use of a control gain which is set by a control gain setting section 8e, so as to reduce an error between the force detected by the load cell 1 and a target force given from a signal generator 8d of the control section 8 to zero. The hydraulic actuator 3 is servo-controlled by the servo feedback control system to adjust a force (more generally, load) applied to the test piece S.

Figure 2:
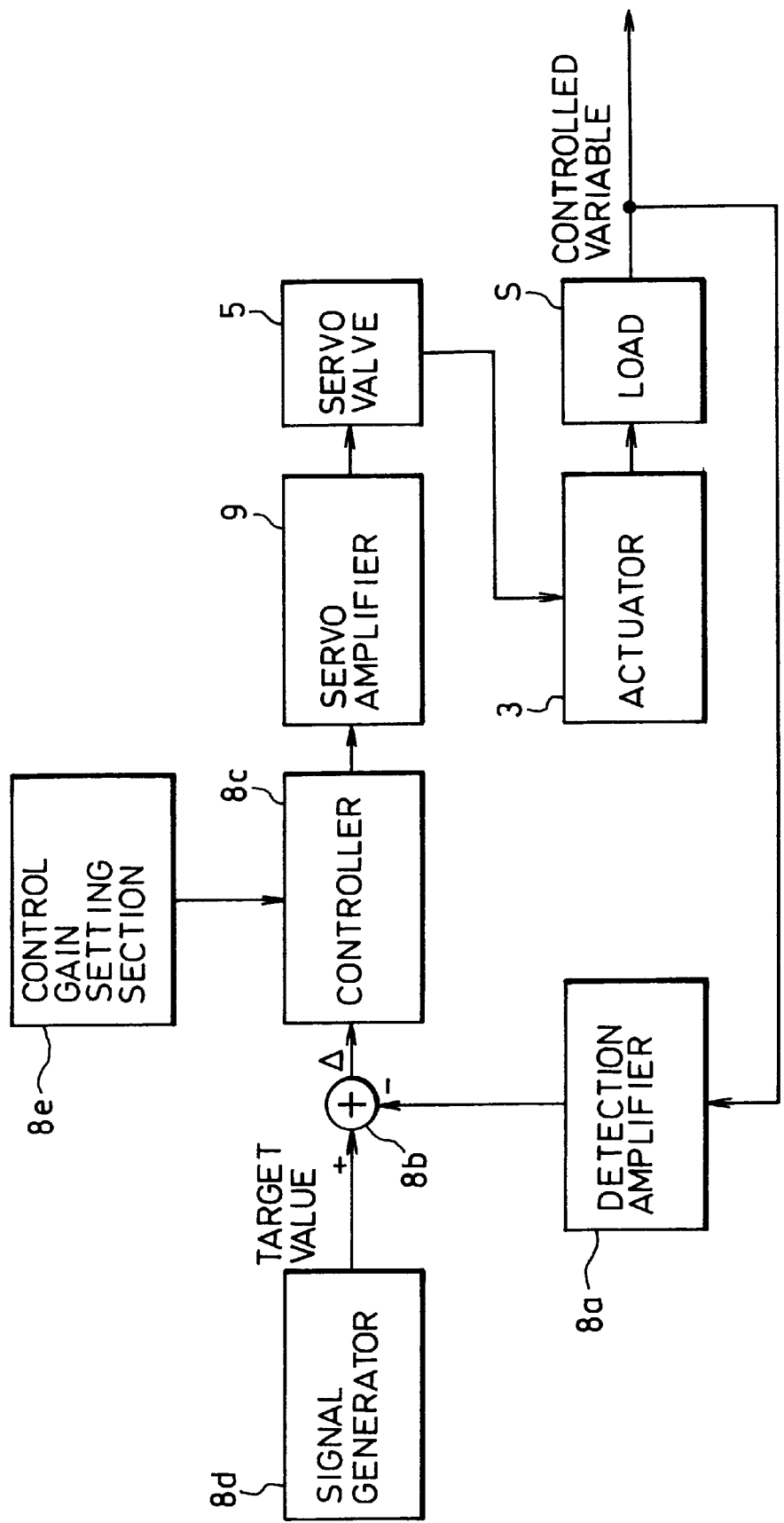
FIG. 2 is a block diagram showing a control loop in the testing machine shown in FIG. 1.

The electrohydraulic servo control system is represented by a feedback control loop, as shown in FIG. 2. More specifically, the control system comprises an error unit 8b for determining an error Δ between a control objective value (a target load or a target displacement, for example) and an output of a detection amplifier 8a which indicates a change (an actual force or an actual displacement) generated in the test piece S, and a controller 8c for controlling, via a servo amplifier 9, the operation of the servo valve 5 in accordance with the error determined by the error unit 8b. Thus, the control system controls the operation of the servo valve 5 so as to reduce the error Δ to zero, thereby hydraulically driving the actuator 3 to adjust the load applied to the test piece S.

The material testing machine of this embodiment serves as a fatigue testing machine. A first feature of the testing machine resides in that, as shown in FIG. 3, the control section 8 comprises a control system 312 for feedback-controlling the load applied from the actuator 3 of the servo system 11 to the test piece S in accordance with the error between the controlled variable and the control target value, and further comprises a correction control system 313 for correcting the control target value per se in accordance with the controlled variable.

The control system 312 is realized by a force control system for generating the control output value $U_K$ to be supplied to the servo system 11 in accordance with the error $\Delta e_K$ between the actual force K and the target force $R_K$, or by a displacement control system for generating the control output value $U_H$ for the servo system 11 in accordance with the error $\Delta e_H$ between the actual displacement H and the target displacement $R_H$.

The correction control system 313 comprises a peak detecting section and a bottom detecting section for respectively detecting a peak value and a bottom value of the controlled variable (actual force K or actual displacement H) in one load changing cycle, while a load condition in which the test piece S is placed is caused to vary at intervals of cycle by changing the control target value (target force $R_K$ or target displacement $R_H$) at intervals of this cycle. Furthermore, the correction control system 313 comprises an amplitude error calculating section 323 for determining, as mentioned later, an actual error between the controlled variable and the control target value within one load condition changing cycle, in accordance with the peak value and the bottom value of the controlled variable; a correction calculating section 324 for determining a correction value for the control target value in accordance with the actual error; and a target value correcting section 325 for correcting the target control value with use of the correction value for every changing cycle of the control target value.

Figure 3:
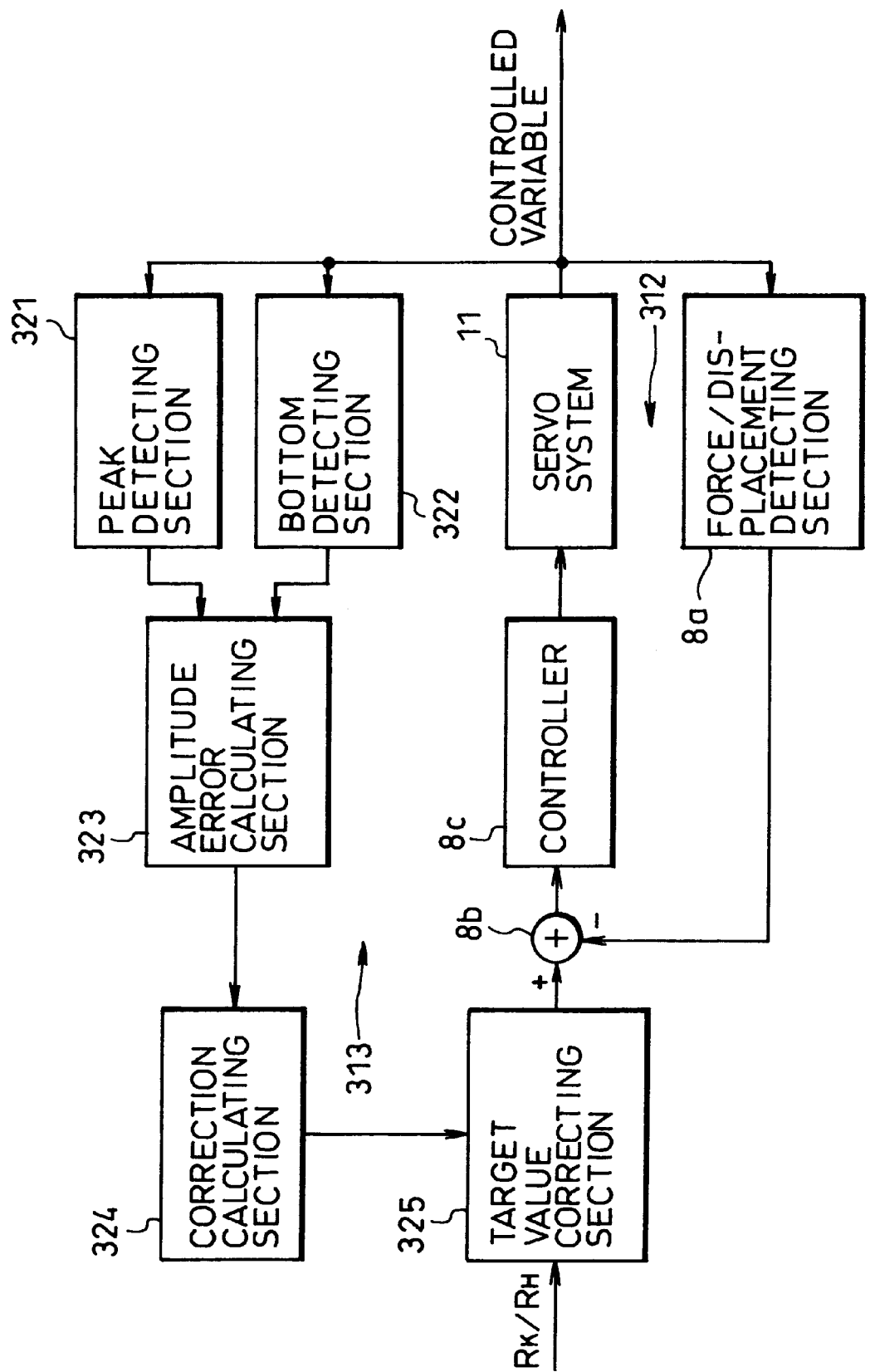
FIG. 3 is a block diagram showing a control system and a correcting control system of the material testing machine.

In FIG. 3, the detection amplifier (force/displacement detecting section) 8a detects the actual force K or the actual displacement H, which is the controlled variable, of the test piece S. The error unit 8b determines the error $\Delta e_K$ between the target force $R_K$ and the actual force K or determines the error $\Delta e_H$ between the target displacement $R_H$ and the actual displacement H. The controller 8c generates the control output value $U_K$ or $U_H$ for the servo system 11 with use of a predetermined control gain and in accordance with the error $\Delta e_K$ or $\Delta e_H$, to thereby control the operation of the servo system 11.

More specifically, in case that the control system 312 is realized by the force control system, the controller 8c determines the control output value $U_K$ with use of the proportional control gain $P_K$ and the integral control gain $I_K$ which are set depending on the elastic constant of the test piece S and in accordance with the following formula (11). On the other hand, if the control system 312 is realized by the displacement control system, the control output value $U_H$ is determined in accordance with the following formula (12) and with use of the proportional control gain $P_H$ and the integral control gain $I_H$ suited to the elastic constant of the test piece. In the following formulas, symbols $\Sigma K$ and $\Sigma H$ denote the integrals of the errors $\Delta e_K$ and $\Delta e_H$, and represent the integral terms in PI control, respectively.

$$U_K = P_K \cdot \Delta e_K + I_K \cdot \Sigma K \qquad (11)$$

$$U_H = P_H \cdot \Delta e_H + I_H \cdot \Sigma H \qquad (12)$$

As seen from formulas (11) and (12), the feedback control in this embodiment is realized by PI control which corresponds to PID control in which the differential term is set to zero. By setting a differential control gain, PID control may be made. The control for the servo system 11 by means of the controller 8c is executed at intervals of an operation cycle, e.g., 100 μsec, at which the control arithmetic operation is carried out by a microprocessor which mainly constitutes the controller 8c.

In case that a fatigue test for the test piece S is performed while controlling the operation of the servo system 11 under the control of the control system 312 constructed as mentioned above, a signal waveform, varying in a specific pattern at intervals of a predetermined cycle, such as a sinusoidal wave or triangular wave, is generally employed as a control target value. The cycle (testing frequency) and amplitude (width) with which the control target value varies are set in dependence on the testing purpose. In a hydraulic servo-controlled fatigue testing machine, the changing cycle (testing frequency) is variably set within a broad range ranging, e.g., from about 0.001 Hz to 100 Hz, depending on the stiffness (elastic characteristic) of the test piece S.

Figure 4:
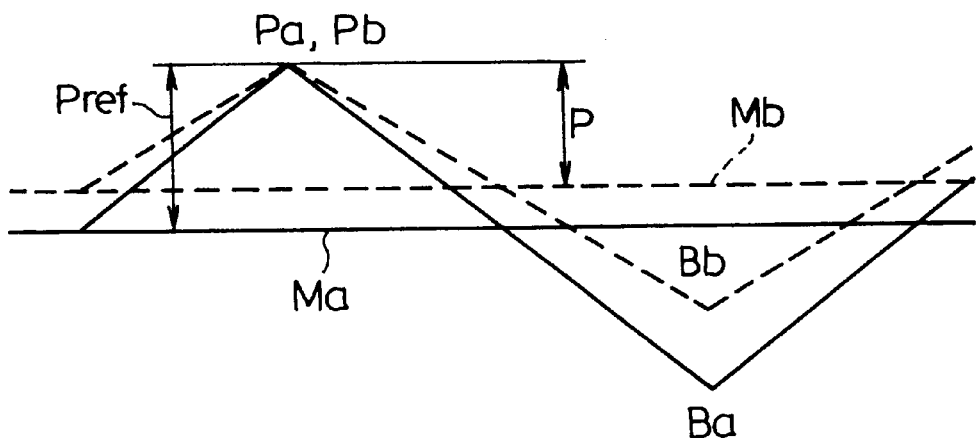
FIG. 4 is a graph showing a relationship between controlled variable and target load in the control system shown in FIG. 3.

When the control target value comprised of such a signal wave which cyclically varies is supplied to the control system 312, a load condition in which the test piece S is placed naturally varies with a change in the control target value, so that the controlled variable (force or displacement) also varies. If the control target value changes at intervals of a short cycle, i.e., if the load condition cyclically changes at a high frequency, a change in the controlled variable (force applied to the test piece or displacement of the test piece), shown by the dotted line in FIG. 4, becomes sometimes smaller than a change in the control target value, shown by the solid line in FIG. 4, which is represented by a triangular signal waveform and is supplied to the control system. Such a deteriorated control response results from the frequency response characteristic of the hydraulic servo system 11, and becomes significant as the frequency at which the load condition varies becomes higher.

In this embodiment, to compensate for the deterioration in control response, the aforementioned peak detecting section 321 and the bottom detecting section 322 detect the peak value Pb and the bottom value Bb of the controlled variable (actual force K or actual displacement H) in one load condition changing cycle, respectively. The amplitude error calculating section 323 determines the actual average force value Mb based on the actual peak value Pb and the actual bottom value Bb, and determines the actual amplitude (mesial amplitude) P of the force applied to the test piece, in accordance with the following formulas:

$$Mb=(Pb+Bb)/2 \qquad (13),$$

$$P=(Pb-Bb)/2 \qquad (14).$$

The peak and bottom values of the control target value (target force) are represented by symbols Pa and Ba, respectively, and the target amplitude Pref and the average value Ma of the target force are given by:

$$Pref=(P-B)/2 \qquad (15),$$

$$Ma=(Pa-Bb)/2 \qquad (16).$$

The amplitude error calculating section 323 determines the actual error $\Delta P$ on the basis of the actual amplitude P determined in one load condition changing cycle and the target amplitude Pref of the signal wave serving as the control target value, in accordance with the following formula.

$$\Delta P = Pref - P \qquad (17)$$

The actual error $\Delta P$ is supplied to the correction calculating section 324 which is realized by PI control system.

The correction calculating section 324 generates a control output value C(PB) used to correct the control target value, with use of a control gain which is set in accordance with the elastic constant of the test piece S. In the case of a force control system, the control output value $C_K(PB)$ is determined, with use of the proportional control gain $P_K(PB)$ and the integral control gain $I_K(PB)$, as shown below:

$$C_K(PB)=P_K(PB)\cdot\Delta P+I_K(PB)\cdot\Sigma\Delta P \qquad (18a).$$

In the case of a displacement control system, the control output value $C_H(PB)$ is determined based on the proportional control gain $P_H(PB)$ and the integral control gain $I_H(PB)$, as shown below:

$$C_H(PB)=P_H(PB)\cdot\Delta P+I_H(PB)\cdot\Sigma\Delta P \qquad (18b)$$

The target value correcting section 325 corrects the control target value R for every changing cycle of the control target value based on the control output control value C(PB), as shown below:

$$R_K'=R_K\cdot(1+C_K(PB)) \qquad (19a)$$

$$R_H'=R_H\cdot(1+C_H(PB)) \qquad (19b)$$

The corrected control target value R' ($R_K'$ or $R_H'$) is supplied to the control system 312.

By supplying the control target value corrected in accordance with the controlled variable (actual value) to the control system 312, it is possible to effectively cause the load condition in which the test piece S is actually placed to coincide with an intended condition, whereby the deterioration in control response of the hydraulic servo system 11 can be effectively compensated. In other words, by increasing the control target value per se in dependence on the actual value, i.e., the controlled variable, in advance such as to compensate for a reduction in load caused by the deteriorated control response, it is possible to supply the control target value which can cancel out the load reduction to the control system 312, thereby making it possible to apply an intended load to the test piece S accurately As a consequence, the load condition for the test piece S can be specified accurately, irrespective of the control response of the servo system 11, even if the load condition varies at intervals of a short cycle, so that a fatigue test can be made with high accuracy, while changing the amplitude of force in an intended width.

Basically, the control section 8 of the testing machine of this embodiment is so configured as to feedback-control the operation of the servo system 11, with use of a predetermined control gain, in accordance with the error between the controlled variable (force or displacement) detected through the detection amplifier 8c and the control target value indicated by a testing waveform supplied from a waveform generator and varying in dependence on the type of material testing, so that the force or displacement varying in accordance with the testing waveform is given to the test piece S.

Figure 6:
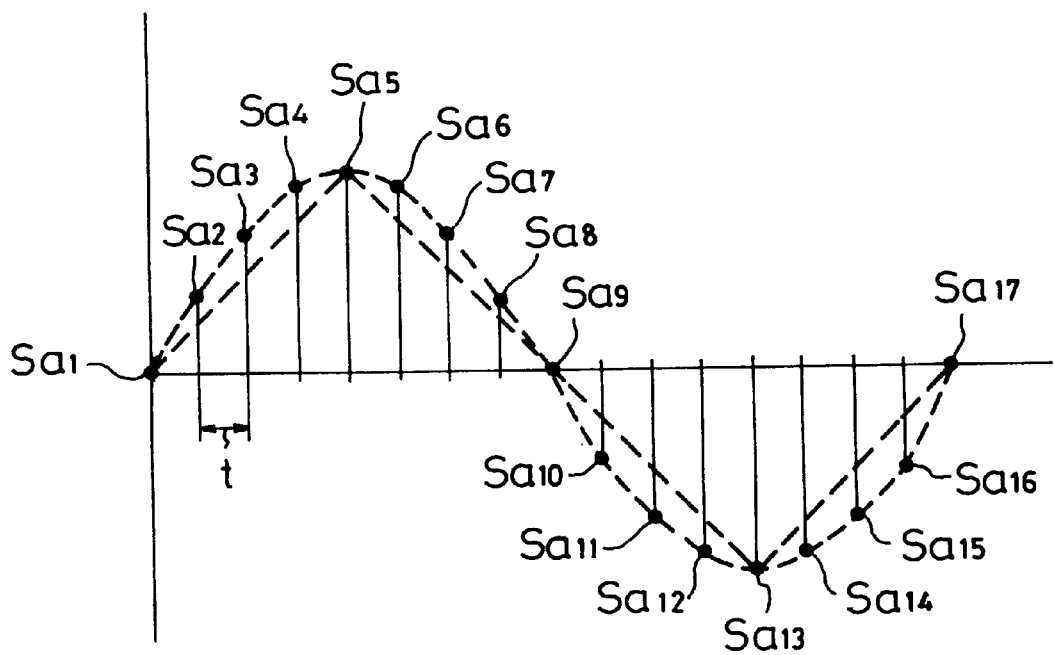
FIG. 6 is a graph showing a relationship between a basic waveform of sinusoidal wave and basic signal values sampled therefrom and stored in a waveform data memory shown in FIG. 5.
Figure 5:
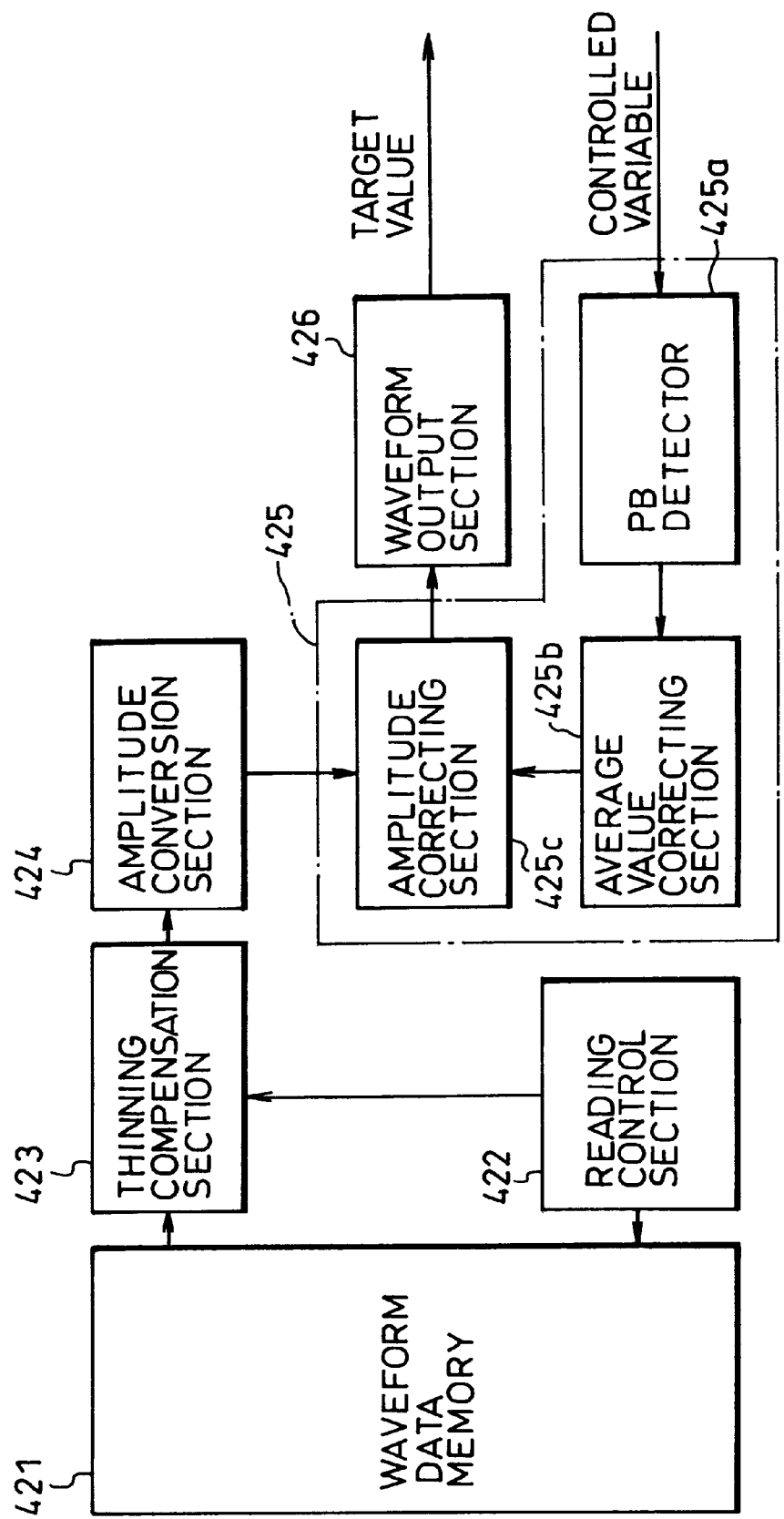
FIG. 5 is a block diagram showing a waveform generator of the material testing machine.
Figure 7:
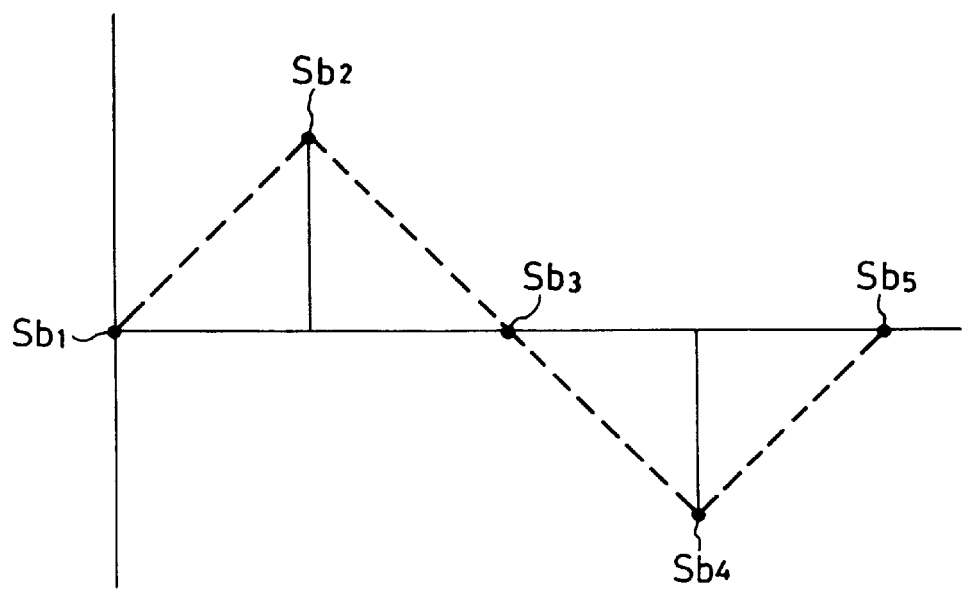
FIG. 7 is a graph showing a relationship between a basic waveform of triangular wave and basic signal values.
Figure 8:
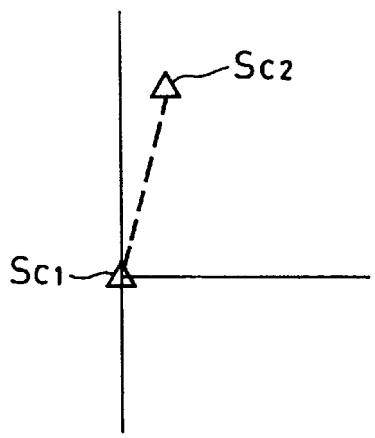
FIG. 8 is a graph showing a relationship between a basic waveform of ramp wave for tensile test and basic signal values.
Figure 9:
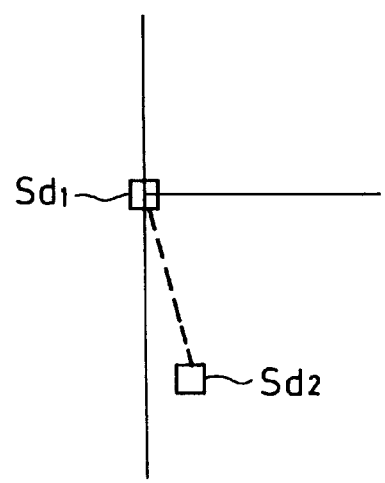
FIG. 9 is a graph showing a relationship between a basic waveform of ramp wave for compression test and basic signal values.

As shown in FIG. 5, the waveform generator which constitutes a second feature of the testing machine comprises a waveform data memory 421 storing therein a series of basic signal values which constitute one cycle part of a normalized basic signal waveform and which are sampled from a basic waveform such as to pick up a characteristic of the basic waveform, such as sinusoidal wave, triangular wave or the like used in material testing. More specifically, the waveform data memory 421 stores, e.g., a series of basic signals Sa1, Sa2, Sa3, . . . , Sa16 and Sa17 sampled from a sinusoidal basic waveform (shown by a dotted line in FIG. 6) which is normalized to have a predetermined signal level. These basic signals are sampled at 17 sampling points, which are spaced at regular time intervals, such as to pick up a characteristic of the sinusoidal basic waveform, and constitute one cycle part of the sinusoidal basic waveform. A triangular basic waveform is represented by a series of basic signal values Sb1, Sb2, . . . , Sb5 sampled from the triangular basic waveform at five sampling points and constituting one cycle part of the triangular basic waveform, as shown in FIG. 7. A basic waveform of ramp wave is represented by two basic signal values Sc1 and Sc2 or Sd1 and Sd2 which specify the start and terminal ends of the ramp wave, as shown in FIGS. 8 and 9. Alternatively, these basic waveforms may be stored in the form of a series of, e.g., 17 basic signal values, as in the case of a sinusoidal basic waveform.

Further, a reading control section 422 is provided, which operates to sequentially read out a series of basic signal values from the waveform data memory 421, these basic signal values indicating a basic signal of a kind selected in dependence on the type of material testing. More specifically, the reading control section 422 reads out the basic signal values at intervals of a predetermined reading cycle from the memory 421.

The waveform generator of this embodiment is configured to generate a testing waveform of a desired type based on an associated basic waveform. In general, the frequency of the intended testing waveform differs from the frequency of the basic waveform. If the basic signal values are read out from the data memory 421 at intervals of the aforementioned reading cycle, only a signal waveform similar to the basic waveform and having a frequency fixedly determined by the reading cycle and the sampling cycle is reproducible. As for the testing waveform having a frequency lower than the frequency of the basic waveform, the number of signal values which constitute the testing waveform is larger than the number of the basic signal values which constitute the basic waveform. That is, the testing waveform of this kind is regarded as being comprised of signal values corresponding in waveform phase to the sampling points at which the basic signal values are sampled from the basic signal and other signal values not corresponding in phase to the sampling points in respect of the basic signal values. Hereinafter, those signal values not corresponding to the sampling points of the basic signal values are referred to as "thinned signal values" or "signal values at thinned sampling points." Further, the number of the thinned signal values between those adjacent two signal values of the testing waveform which correspond to the associated two sampling points of the basic signal values is referred to as "thinning number." The thinning number is determined in dependence on the frequency of the testing waveform, the reading cycle, and the number of sampling of the basic signal values from the basic waveform.

On an occasion that the basic signal values are read out from the data memory 421 at intervals of the predetermined reading cycle, the reading control section 422 repeatedly reads out each of the basic signal values a repetitive number of times determined by the thinning number.

For example, a testing waveform serving as the control target value can have the frequency which is one-third of the frequency of a signal wave constituted by a series of signal values obtained by reading out 16 basic signal values, which constitute one cycle part of the basis waveform, at intervals of the reading cycle from the data memory 421. In this case, the series of the basic signal values must be read out from the data memory 421 at intervals of a cycle which is three times longer than the reading cycle. In this connection, the reading control section 422 regards the series of the basic signal values stored in the memory 421 as corresponding to a thinned testing waveform which is comprised of one-third of those signal values required to generate or reproduce the intended testing waveform.

Figure 10:
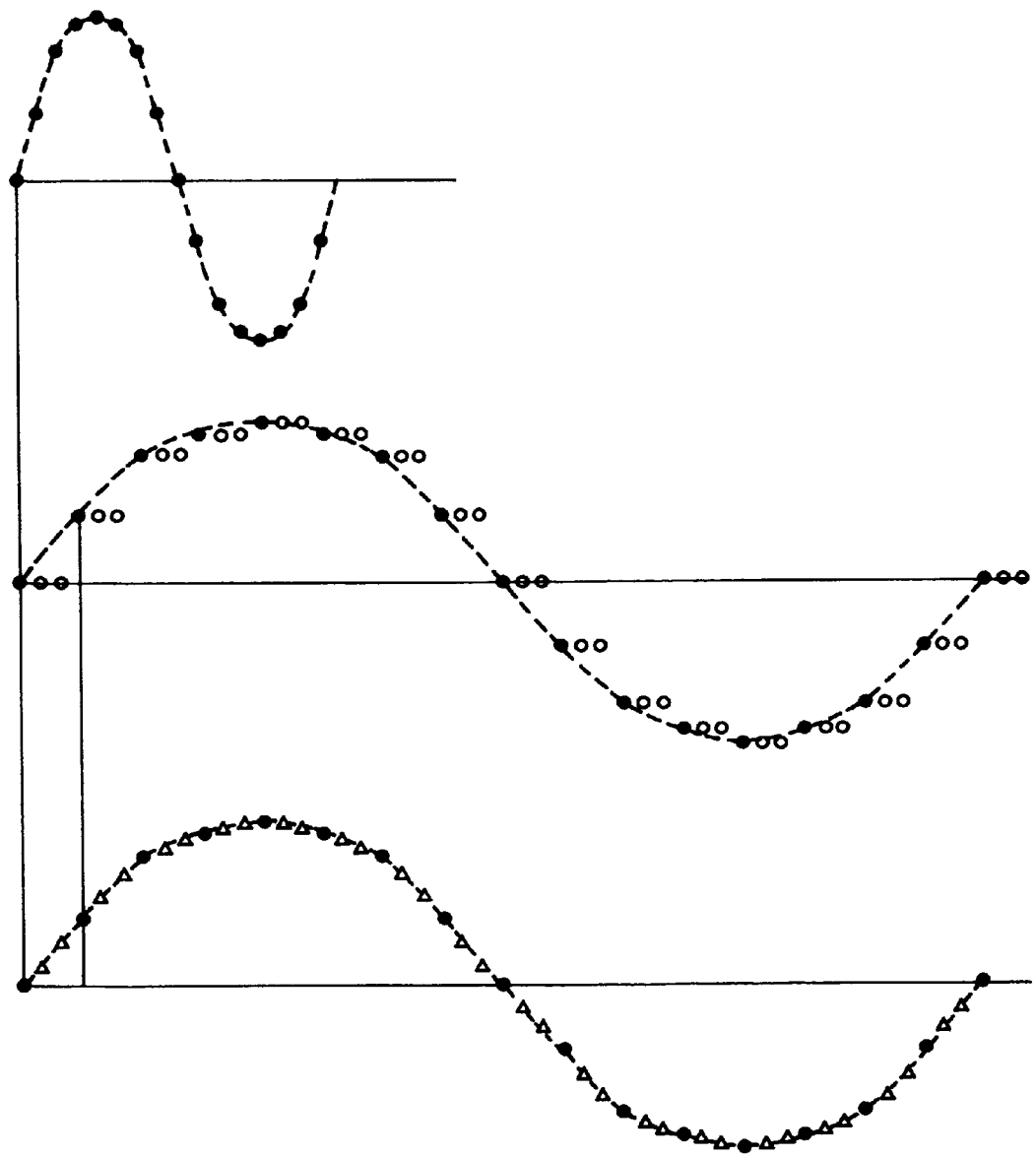
FIG. 10 is a graph showing basic signal values stored in the waveform data memory and sampled from a basic waveform, temporary signal values read out from the waveform data memory, and signal values obtained by subjecting the temporary signal values to thinning compensation and constituting a temporary testing waveform.

To obtain signal values at thinned sampling points, the reading control section 422 reads out each of the basic signal values, stored in the data memory 421 as shown in upper part of FIG. 10, three times as shown in the middle part of FIG. 10, to thereby obtain a required number of temporary signal values for reproduction of a testing waveform having an intended frequency. These temporary signal values include ones corresponding in phase to the sampling points at which the basic signal values are sampled, and further include those temporary signal values corresponding in phase to the thinned sampling points in respect of the testing waveform and not corresponding to the basic waveform sampled points.

A thinning compensation section 423 is provided, which operates to correct those ones of the temporary signal values read out from the waveform data memory 421 which correspond to the thinned sampling points, to thereby obtain a temporary testing waveform shown in the lower part of FIG. 10. The temporary testing waveform is similar in shape to the basic waveform and has the same frequency as that of the testing waveform.

Figure 11:
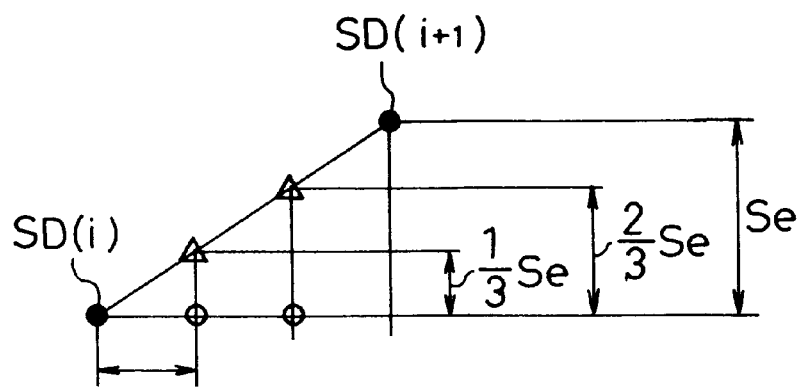
FIG. 11 is a graph showing thinning compensation processing for the temporary signal values.

The thinning compensation is carried out based on the thinning number n and the difference e between two temporary signal values SD(i) and SD(i+1) respectively corresponding to two basic signal values sampled at the basic waveform sampled points i and i+i+1, as shown in FIG. 11. More specifically, the difference e between the aforementioned two temporary signal values is generated during the period of time which corresponds to n+1 sampling points, including n thinned sampling points, in respect of the testing wave form. Thus, a correction value for the first thinned sampling point is calculated in accordance with the following formula.

$$[\text{correction value}] = \{SD(i+1) - SD(i)\}/(n+1)$$

For the thinning compensation in respect of other thinned sampling points, an accumulated correction value is employed which is obtained by multiplying the correction value by the number by which the associated basic signal value SD(i) is repeatedly read out from the data memory 421 until the temporary signal value at the intended thinned sampling point is acquired. As shown in the middle part of FIG. 10, a series of temporary signal values are obtained by repeatedly reading out each basic signal value a repetitive number of times, represented by the sum of the thinning number and a value of 1. By subjecting the series of the temporary signal values to the aforementioned correction, these temporary signal values are subject to thinning-compensation, whereby a temporary testing wave which is similar in shape to the basic waveform and which has the same frequency as that of the intended testing waveform is generated.

The temporary testing waveform generated in the thinning compensation section 423 is supplied to an amplitude conversion section 424 in which the temporary testing waveform is subject to, e.g., coefficient processing to adjust the amplitude level of the temporary testing waveform, in order to obtain the testing waveform to be supplied as a control target value to the control section 8. The thus amplitude-corrected signal waveform(series of signal values) is supplied through a correction circuit 425, mentioned later, to a waveform output section 426. The amplitude-corrected signal waveform is subject to smoothing processing in the waveform output section 426, where required, to be output to the control section 8 as the testing waveform.

In the case of generating a waveform of a type varying in a specific pattern at intervals of a predetermined cycle, such as a sinusoidal wave, triangular wave or the like, the temporary testing waveform can be generated by reading out cyclically, at intervals of the same cycle as that of the specific pattern, a series of basic signal values which constitute the basic waveform. In the case of generating a waveform such as a ramp waveform, while repeatedly reading out the first basic signal value which cooperates with the final basic signal value to represent the ramp waveform, to thereby generate temporary signal values at the thinned sampling points, each temporary signal value is subject to the thinning compensation in which each temporary signal value is compensated with use of an accumulated correction value which is determined by the difference e between the first and final basic signal values and the number of times by which the first basic signal value is repeatedly read out until this temporary signal value is acquired. In the case of a ramp-hold waveform, the reading-out and thinning-compensation processing is performed as in the case of a ramp waveform, and thereafter, the basic signal value finally read out is kept maintained.

According to the waveform generator constructed as mentioned above, even if pieces of sampled data, i.e., the basic signal values, stored in the waveform data memory 421 and indicative of the basic waveform, are small in number, each of the basic signal values is repeatedly read out a number of times, determined depending on the frequency of the testing waveform to be generated, while a series of the basic signal values are read out at intervals of a predetermined cycle from the data memory 421, whereby temporary signal values at thinned sampling points are acquired. Then, these temporary signal values are corrected in accordance with the thinning number, whereby the intended testing waveform can be generated with high accuracy even if the testing waveform has a low frequency. In addition, the testing waveform can be generated by adjusting the amplitude of a temporary testing waveform having a desired frequency and obtained by subjecting the temporary signal values to the thinning compensation. Thus, signal processing for generation of the testing waveform is extremely simplified, and hence an accurate testing waveform can be generated with use of a simplified arrangement.

The correction circuit 425 corrects the testing waveform, generated in the above manner, in accordance with the controlled variable. More specifically, since the servo system has a proper frequency response characteristic, even if the testing waveform suited to the intended material testing and indicative of control target value is supplied to the servo system, the actual force or displacement which coincides with the target force or displacement represented by the control target value is not always obtainable. In other words, even if the testing waveform, generated with the intention of applying a force, which periodically varies with a certain amplitude, to the test piece S, is supplied to the control section 8, the force actually applied to the test piece S is sometimes deviated from a desired one.

Figure 12:
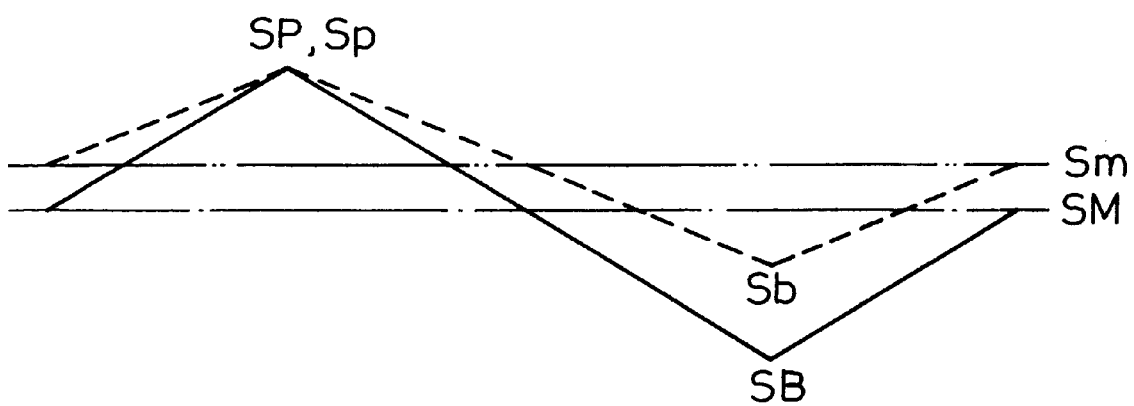
FIG. 12 is a graph showing a parameter which relates to a controlled variable-based correction to the testing waveform.

To eliminate the error in a testing condition caused by the frequency response characteristic of the servo system, the waveform generator comprises a correction circuit 425 for correcting the testing waveform obtained in the above manner, so as to generate a more appropriate testing waveform. The correction circuit 425 includes a PB detector 425a for detecting a peak and bottom values of the controlled variable, e.g., actual force or actual displacement; and an average value correcting means 425b for determining an average value Sm of the controlled variable, as shown in FIG. 12, based on the peak value Sp and the bottom value Sb of one cycle part of the controlled variable, detected by the PB detector 425a, and for determining a correction amount for the control target value based on the difference between the average value Sm of the controlled variable and an average value SM of the target force indicated by the control target value. In FIG. 12, symbols SP and SB respectively indicate the peak and bottom values of the target force. Further, the correction circuit 425 includes an amplitude correcting section 425c for inputting the testing waveform having been subject to the amplitude level adjustment in the amplitude conversion section 424. The amplitude correcting section 425 corrects the amplitude and average value of the testing waveform in accordance with the correction value determined by an average value correcting means 425b, to thereby adjust the amplitude per se of the testing waveform such that the force applied to the test piece S has a desired amplitude which satisfies the intended material testing condition.

In this embodiment, if the force actually applied to the test piece S varies as shown by the dotted line in FIG. 12 despite that the testing waveform (control target value) shown by the solid line in FIG. 12 is supplied, the testing waveform is corrected in accordance with the controlled variable by means of the aforesaid amplitude adjustment of the testing waveform effected by the correction circuit 425, whereby the material testing condition (e.g., force condition) for the test piece S can be specified with high accuracy. As a consequence, the material testing can be made highly accurately with use of the testing waveform easily generated, to thereby improve the testing accuracy. In particular, since the amplitude-corrected testing waveform, acquired by directly correcting the amplitude of the testing waveform after subjected to amplification conversion, is output as a control target value, the material testing accuracy can be improved easily and efficiently.

The present invention is not limited to the foregoing embodiment but may be modified in various manners.

For instance, the control target value can be corrected on the basis of an average error value determined from the peak and bottom values of the controlled variable. More specifically, in order to correct the control target value, an average error value $\Delta m$ is determined based on an average value Ma of the control target value and the actual average value Mb of the controlled variable, and an average value M of a new control target value is determined with use of a predetermined control gain Km, as shown below:

$$M = Ma + Km \cdot \Sigma \Delta m.$$

Furthermore, the average value M of the control target value may be used in combination with the aforementioned correction of the control target value, to correct the target value supplied to the control system 312.

It is preferable to increase the number of sampling points to attain the basic signal values, as long as these values can be stored in the waveform data memory 421 in light of the memory capacity. The thinning number n which determines the repetition number of times for which each basic signal value is repeatedly read out from the data memory 421 may be determined in accordance with the basic frequency and the frequency of the testing waveform given as control target value. The basic frequency is determined by the sampling number of times for which the basic wave is sampled and the reading frequency at which the basic signal values are read out from the data memory 421. If the basic frequency is equal to the frequency of the testing waveform, the thinning number n is set to zero, so that no thinning processing is performed.

The testing waveform may be obtained by reading a random waveform, other than the basic waveform and acquired at the outside of the testing machine, into the control section 8 and by processing the random waveform as in the case of the basic waveform, and may be employed as a target value in the feedback control.

It is understood that the present invention may be further modified without departing from the scope or spirit of the invention.

What is claimed is:

1. A material testing machine for measuring a mechanical property of a test piece based on a load given to the test piece and a mechanical change generated in the test piece, while feedback-controlling an operation of a servo system, including a hydraulic actuator which gives the load to the test piece, by means of a controller, such that an actual load applied to the test piece coincides with a target load, comprising:

load controls means for periodically changing a target load in the feedback control to thereby periodically change a load given to the test piece;

error detection means for determining at least one of an amplitude and an average value of a controlled variable in the feedback control, for every target load changing cycle, based on a peak value and a bottom value of the controlled variable which changes with a change in the load, and for determining at least one of first and second errors based on at least one of the amplitude and the average value of the controlled variable and at least one of an amplitude and an average value of the target load, the first error being an error between the amplitude of the controlled variable and the amplitude of the target load, the second error being an error between the average value of the controlled variable and the average value of the target load; and correction means for correcting at least one of the amplitude and the average value of the target load in accordance with at least one of the first and second errors determined by said error detection means.

2. A material testing machine for measuring a mechanical property of a test piece based on a load given to the test piece and a mechanical change generated in the test piece, while feedback-controlling an operation of a servo system, including a hydraulic actuator which gives the load to the test piece, by means of a controller, such that actual load applied to the test piece coincides with target load, comprising:

load controls means for periodically changing a target load in the feedback control to thereby periodically change a load given to the test piece;

error detection means for determining at least one of an amplitude and an average value of a controlled variable in the feedback control, for every target load changing cycle, based on a peak value and a bottom value of the controlled variable which changes with a change in the load, and for determining at least one of first and second errors based on at least one of the amplitude and the average value of the controlled variable and at least one of an amplitude and an average value of the target load, the first error being an error between the amplitude of the controlled variable and the amplitude of the target load, the second error being an error between the average value of the controlled variable and the average value of the target load;

correction means for correcting at least one of the amplitude and the average value of the target load in accordance with at least one of the first and second errors determined by said error detection means;

a waveform generator for generating a testing waveform which indicates a target load in the feedback control, wherein said waveform generator includes:

a waveform data memory storing therein a series of basic signal values which are sampled from a basic waveform so as to pick up a characteristic of the basic waveform;

waveform data reading means for reading out the series of basic signal values from said waveform data memory and for repetitively reading out at least one basic signal value a repetitive number of times which is determined by a thinning number, to thereby obtain temporary signal values;

thinning compensation means for correcting, in accordance with the thinning number, those temporary signal values which do not correspond to any of sampling points at which the basic signal values are sampled from the basic waveform, to thereby obtain a temporary testing waveform which is similar in shape to the basic waveform; and testing waveform generator means for adjusting an amplitude of the temporary testing waveform to thereby obtain a testing waveform.

3. The material testing machine according to claim 2, wherein said waveform data memory stores therein the series of basic signal values which constitute one cycle part of the basic waveform;

the thinning number is set in accordance with a number of times of sampling the series of basic signal values from the basic waveform, the frequency of the testing waveform, and the cycle at intervals of which said waveform reading means reads out the basic signal values; and the thinning compensation means obtains the temporary testing waveform which has the same frequency as that of the testing waveform.

4. The material testing machine according to claim 2, wherein said thinning compensation means corrects each of temporary signal values which do not correspond the sampling points of the basic waveform, based on a compensation value which is determined in accordance with the thinning number and the difference between two temporary signal values associated therewith among the temporary signal values corresponding to the sampling points of the basic waveform.

5. The material testing machine according to claim 3, wherein said waveform generator further includes testing waveform level setting means for variably setting a level of an average value of the testing waveform in accordance with the controlled variable fed back to the controller.

* * * * *